May 14, 1946. A. CUMMING Plant Pat. 689
CHRYSANTHEMUM PLANT
Filed Sept. 24, 1945
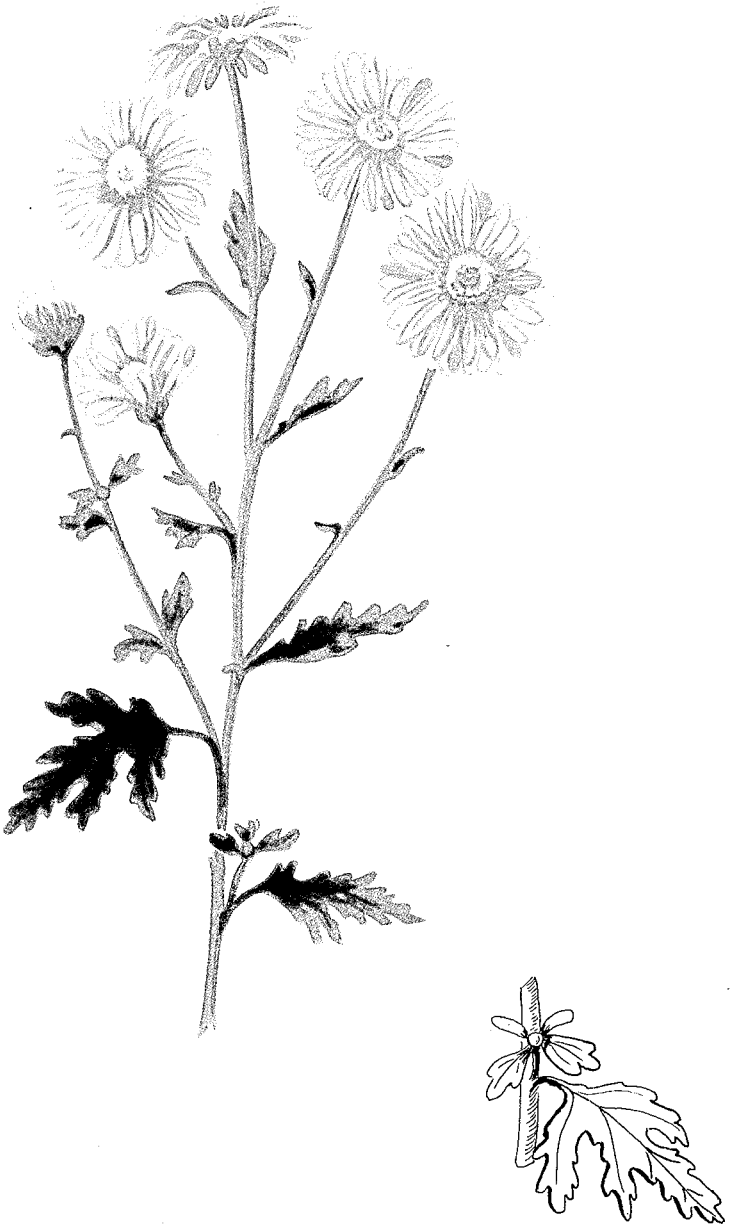
INVENTOR
Alexander Cumming
By Orville M. Kile
Plant Pat. Agt.

Patented May 14, 1946

Plant Pat. 689

UNITED STATES PATENT OFFICE

689

CHRYSANTHEMUM PLANT

Alexander Cumming, Bristol, Conn., assignor to Bristol Nurseries, Inc., Bristol, Conn., a corporation of Connecticut Application September 24, 1945, Serial No. 618,113

1 Claim. (Cl. 47—60)

My present invention relates to a new and distinct variety of chrysanthemum plant, producing semi-double flowers. This is a distinctly summer-blooming variety, providing a continuous display of effective color during the trying summer months when color is definitely needed. Although a heat-resisting variety it is also more winter-hardy and better adapted to over-wintering under varying conditions than any chrysanthemum variety of which I know.

This new variety is the result of definite breeding efforts carried on by me and was obtained from seed produced by self-fertilization of a seedling chrysanthemum which in turn had resulted from three generations of interbreeding from the original cross—Pomponette × Dwarf *Chrysanthemum arcticum* seedling.

The accompanying illustration shows a branch of the flowers of this new variety in August, in as true colors as the artist could portray them. Also shown in the illustration is a black-and-white drawing of a portion of a stem, indicating how the supplementary buds are formed in the leaf axils.

In the following detailed description, color plate numbers refer to Ridgway's Color Standards and Nomenclature. Other references to color indicate the ordinary dictionary term.

*The plant*

Growth habits: Extremely bushy, with many slender, upright, shrublike stems. Average height of a full-grown plant is about 2 feet.

Development habits: This variety is more permanent, requiring less division than any other known variety. It is distinctly heat-resisting and also very winter-hardy.

Blooming season: Commences flowering about July 1st in this climate and continues through September, flowering effectively the entire season.

Stems: Slender, wiry, long, Light Cress Green (Plate XXXI).

Foliage:

*Color.*—Glossy green, approximately Forest Green (Plate XVII) on upper side. Under side is Light Bice Green (Plate XVII).

*Size.*—Small. Full grown leaf is ¾ to 1½ inches wide by 1½ to 2½ inches long.

*Shape.*—Palmately divided into five main lobes which are deep and rather sharply toothed.

*Petiole.*—Length is ½ inch or less.

*The flower*

Bud: Small, flat. Opens slowly.

Flower:

*Form.*—Composite flower consisting of 2 or 3 rows (average 40) of ray flowers or petals about ¾ inch long, extending in a horizontal position around an open center or cushion composed of upwards of 200 individual florets about ⅛ inch long.

*Color.*—Approximately Lemon Yellow (Plate IV) on the upper surface and slightly lighter on the reverse side. Center of newly opened flower is flat and greenish in the middle. Later the florets in the center open, producing a raised cushion of golden yellow. The color effect is particularly brilliant during the periods of hot weather which are detrimental to the average chrysanthemum.

*Size.*—From 1½ to 2½ inches in diameter.

*Fragrance.*—Moderate.

*Lasting quality as cut flower.*—Excellent.

*Comparison*

The variety most like my new variety is Acacia, but the two differ principally as follows:

1. My new variety begins flowering earlier (about July 1st in Connecticut) and continues effective flowering throughout a much longer season.
2. The blossoms of my new variety are larger.
3. There are fewer blossoms of my variety to a spray.
4. Stems of my variety are more wiry and erect.
5. The plant of my variety is much more winter-hardy.
6. The plant of my variety is more permanent and requires less division.

Having thus disclosed my invention, I claim:

The new and useful variety of chrysanthemum plant substantially as shown and described, characterized particularly by its bushy growth; its permanence and winter-hardiness; and its early and long blooming season in which are continuously produced effective quantities of semi-double, golden-yellow flowers.

ALEXANDER CUMMING.